US012573487B2

(12) United States Patent
Barry

(10) Patent No.: US 12,573,487 B2
(45) Date of Patent: *Mar. 10, 2026

(54) SYSTEMS AND METHODS FOR GENERATING, MANAGING, AND SHARING DIGITAL SCRIPTS

(71) Applicant: ALLSCRIPTS SOFTWARE, LLC, Chicago, IL (US)

(72) Inventor: Zoe Barry, Cambridge, MA (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 213 days.

This patent is subject to a terminal disclaimer.

(21) Appl. No.: 18/100,164

(22) Filed: Jan. 23, 2023

(65) Prior Publication Data

US 2023/0162154 A1 May 25, 2023

Related U.S. Application Data

(62) Division of application No. 13/781,270, filed on Feb. 28, 2013, now Pat. No. 11,562,324.

(Continued)

(51) Int. Cl.
*G06Q 50/00* (2024.01)
*G06Q 10/10* (2023.01)
(Continued)

(52) U.S. Cl.
CPC .............. *G16H 20/10* (2018.01); *G06Q 10/10* (2013.01); *G16H 10/60* (2018.01); *G16H 40/67* (2018.01)

(58) Field of Classification Search
CPC ........ G16H 20/10; G16H 10/60; G16H 40/67; G06Q 10/10
See application file for complete search history.

(56) References Cited

U.S. PATENT DOCUMENTS

| 5,845,255 A | 12/1998 | Mayaud |
| 7,202,972 B1 | 4/2007 | Schwier et al. |

(Continued)

FOREIGN PATENT DOCUMENTS

| AU | 2007/100401 A4 | 6/2007 |
| AU | 2010/101371 A4 | 1/2011 |

(Continued)

OTHER PUBLICATIONS

Anonymous "Prescryption DrugSafe: Architecture Doc" http:// courses.cs.washington.edu/courses/case43/06wi/LCA, 2013.

(Continued)

*Primary Examiner* — Maroun P Kanaan
(74) *Attorney, Agent, or Firm* — CALFEE, HALTER & GRISWOLD LLP

(57) ABSTRACT

The present disclosure generally relates to improved systems and methods for generating, managing, and sharing digital scripts—which are accessible to patients and/or health care providers and may be accepted by any appropriate prescription dispensary—as well as a comprehensive, real-time source of patient prescription history in compliance with and furtherance of the Meaningful Use regulations. The systems and methods may support the multi-directional flow of script information to improve disease monitoring and treatment, to mitigate patient health risks like undesirable drug interactions, to identify social factors like patient ability to afford prescriptions, and to prevent prescription fraud like forged refills.

14 Claims, 10 Drawing Sheets

Related U.S. Application Data

(60) Provisional application No. 61/605,500, filed on Mar. 1, 2012, provisional application No. 61/693,072, filed on Aug. 24, 2012.

(51) Int. Cl.

| | | |
|---|---|---|
| *G06Q 50/22* | (2024.01) | |
| *G16H 10/60* | (2018.01) | |
| *G16H 20/10* | (2018.01) | |
| *G16H 40/67* | (2018.01) | |

(56) References Cited

U.S. PATENT DOCUMENTS

| | | | |
|---|---|---|---|
| 7,426,475 | B1 | 9/2008 | Tangellapally et al. |
| 7,974,924 | B2 | 7/2011 | Holla et al. |
| 8,271,128 | B1 | 9/2012 | Schultz |
| 8,286,071 | B1 | 10/2012 | Zimmerman et al. |
| 9,280,685 | B2 | 3/2016 | Jackson |
| 10,170,204 | B1 | 1/2019 | Eller et al. |
| 2002/0111829 | A1 | 8/2002 | Robibero |
| 2002/0156782 | A1 | 10/2002 | Rubert |
| 2003/0018495 | A1 | 1/2003 | Sussman |
| 2003/0052788 | A1 | 3/2003 | Kwong-Tai Chung |
| 2003/0144874 | A1 | 7/2003 | Barret et al. |
| 2004/0019512 | A1 | 1/2004 | Nonaka |
| 2004/0225528 | A1 | 11/2004 | Brock |
| 2005/0144039 | A1 | 6/2005 | Tamblyn et al. |
| 2006/0031094 | A1 | 2/2006 | Cohen et al. |
| 2006/0149567 | A1 | 7/2006 | Muller et al. |
| 2006/0259330 | A1 | 11/2006 | Schranz |
| 2007/0100834 | A1 | 5/2007 | Landry et al. |
| 2007/0124399 | A1 | 5/2007 | Gillespie et al. |
| 2007/0162309 | A1 | 7/2007 | Denny |
| 2007/0208665 | A1 | 9/2007 | Ohara |
| 2008/0154622 | A1 | 6/2008 | El Kadri et al. |
| 2008/0208626 | A1 | 8/2008 | Greenman |
| 2009/0150292 | A1 | 6/2009 | Trinh et al. |
| 2009/0327363 | A1 | 12/2009 | Cullen et al. |
| 2010/0241444 | A1 | 9/2010 | Young |
| 2010/0262577 | A1 | 10/2010 | Pulfer et al. |
| 2010/0268550 | A1* | 10/2010 | Abuzeni ............... G16H 20/10 |
| | | | 705/2 |
| 2011/0301978 | A1 | 12/2011 | Shiu et al. |
| 2013/0019156 | A1 | 1/2013 | Gonser et al. |
| 2013/0041678 | A1 | 2/2013 | Tayal et al. |
| 2013/0096938 | A1* | 4/2013 | Stueckemann ........ G16H 40/60 |
| | | | 705/2 |
| 2013/0304509 | A1 | 11/2013 | Alexander |

FOREIGN PATENT DOCUMENTS

| | | | |
|---|---|---|---|
| WO | WO-94/25927 | A2 | 11/1994 |
| WO | WO-03/019422 | A1 | 3/2003 |
| WO | WO-2009/006609 | A1 | 1/2009 |
| WO | WO-2010/042954 | A1 | 4/2010 |

OTHER PUBLICATIONS

Chadwick "The Secure Electronic Transfer of Prescriptions" Healthcare Computing Conference: Delivering Health Informatics at the Point of Care, pp. 1-12, 2004.

Communication Pursuant to Article 94(3) EPC issued in European Patent Application No. 13 715 480.3 on Oct. 15, 2020.

Kuo et al "A 2D Barcode Validation System for Mobile Commerce" Advances in Grid and Pervasive Computing, pp. 150-161, 2010.

Nelson et al "Building a Standards-Based and Collaborative E-Prescribing Tool MyRxPad" IEEE International Conference on Bioinformatics and Biomedicine, pp. 210-215, 2009.

Search Report and Written Opinion issued in International Patent Application No. PCT/US2013/028354 on Oct. 28, 2013.

* cited by examiner

SYSTEMS AND METHODS FOR GENERATING, MANAGING, AND SHARING DIGITAL SCRIPTS

RELATED APPLICATIONS

This application is a divisional of U.S. patent application Ser. No. 13/781,270, filed on Feb. 28, 2013, which claims priority to U.S. Provisional Patent Application No. 61/605,500, filed on Mar. 1, 2012, and U.S. Provisional Patent Application No. 61/693,072, filed on Aug. 24, 2012, each of which is incorporated herein by reference in its entirety.

TECHNICAL FIELD

The present disclosure relates generally to systems and methods for implementing and recording healthcare directives and related transactions. More specifically, the present disclosure relates to systems and methods for generating, managing, and sharing a digital script and/or a comprehensive, real-time source of patient prescription history.

BACKGROUND OF THE INVENTION

The U.S. Health Information Technology for Economic and Clinical Health (HITECH) Act, referred to generally as "Meaningful Use," has incentivized medical providers ("providers") to transition patient medical records from paper to electronic formats. Methods and systems enabling the storage and input of electronic patient medical records have been described and are utilized in industry. In addition, Electronic Health Record (EHR) and Electronic Medical Record (EMR) companies offer services designed to enable providers to prescribe medications via Computerized Physician Order Entry (CPOE) software programs. Health care providers utilize these services by entering the necessary information into an interface of a CPOE software program to generate a CPOE script. Unlike a traditional paper script, the CPOE script is never given to a patient. Instead, the CPOE script is transmitted to a designated pharmacy. The patient must go to the designated pharmacy to obtain his or her prescription. Also, instead of being maintained in electronic format, the CPOE script is delivered to the pharmacy via facsimile transmission; that is, a CPOE script is just another version of a paper script.

While electronic delivery systems utilizing CPOE have moderated the human errors associated with paper scripts passed between providers and patients (e.g., illegible, incomplete, or misplaced paper scripts), numerous shortcomings remain due to, for example, the plurality of different EHR and EMR systems employed by different providers and the unidirectional flow of prescription information to pharmacies. Just the transfer of the CPOE script back to paper format via facsimile reintroduces problems of image quality and potential human errors associated with entering information into a pharmacy's own system for tracking scripts.

Direct delivery of CPOE scripts from providers to pharmacies bypasses patients, thus impinging patient ability to inspect a script before filling it at the designated pharmacy and to compile a complete prescription history, particularly when CPOE scripts are transmitted from multiple providers with separate medical recordkeeping. Furthermore, patient choice of pharmacy is dictated by the initial pharmacy designation even if another pharmacy would be more convenient, for example, if a patient is traveling. In effect, a designated pharmacy "owns" the CPOE script and any associated refills. That is, a patient must use and return to the designated pharmacy for prescription refills unless the pharmacy transfers the script to a different pharmacy or a provider generates a new script.

These existing delivery systems utilizing CPOE scripts also result in missed opportunities for providers to provide more efficient and comprehensive care. Because the CPOE script information only flows in one direction (i.e., to designated pharmacies), these systems do not help a provider to compile a complete prescription history for a patient. For example, providers are not informed when a script is filled, refilled, or transferred. Likewise, unless a patient or caregiver makes an effort to inform a provider about scripts from other providers and/or filled at other pharmacies, the provider will not have information (e.g., about potentially undesirable or dangerous drug interactions) that may be important to the patient's health and treatment decisions.

SUMMARY OF THE INVENTION

In compliance with and furtherance of the Meaningful Use regulations, embodiments of the present invention relate to an improved system for creating, updating, and sharing digital scripts—which are accessible to patients and/or health care providers and may be accepted by any appropriate dispensary—as well as a comprehensive, real-time source of patient prescription history. In certain embodiments of the present invention, the system provides for the multi-directional flow of script information to improve disease monitoring and treatment, to mitigate patient health risks like undesirable drug interactions, to identify social factors like patient ability to afford prescriptions, and to prevent prescription fraud like forged refills. These benefits may accrue not only to individual patients but also to patient populations. Embodiments of the present invention may also provide for sharing of patient prescription history across the spectrum of stakeholders (e.g., other providers and caregivers) involved with the care of a patient.

The system of the invention relates to an electronic prescription system for generating, managing, and sharing digital scripts. In certain embodiments, the system comprises a processor for processing data relating to a digital script, including dynamic data and/or static data, a storage medium for storing information relating to the digital script, and instructions executable by the processor that, when executed, cause the processor to merge selected portions of the dynamic data and/or the static data to create a digital script, and apply a security procedure to the digital script to create a secured digital script. In certain embodiments, the security procedure includes encoding and/or encrypting the digital script.

In certain embodiments, the system further comprises an output device to output the secured digital script. The secured digital script may be output to a designated branded user, which may include one or more of a patient, provider, pharmacist, and caregiver. In other embodiments, the secured digital script may be output to a storage device. The system may further include instructions executable by the processor that, when executed, cause the processor to store the secured digital script in the storage medium.

In certain embodiments, the system may further include an interface for communicating with a network database in a computer network and instructions executable by the processor that, when executed, cause the processor to request the dynamic data and/or the static data over the interface from the network database. In other embodiments, the system may include instructions executable by the processor that, when executed, cause the processor to output the secured digital script over the interface to the network database.

In certain embodiments, static data and/or dynamic data may include one or more of: prescription data, an order set, prescription interaction data, a customized medical directive, a diagnosis code, patient data, caregiver data, provider data, pharmacist data, dispensary data, data extracted from an existing digital script, insurance data, payment data, a record of generating a new digital script, a modification to an existing digital script, a record of filling a digital script, and a representation of the number of refills remaining.

In certain embodiments, the system comprises an interface for communicating with a computer network, a processor for processing data relating to a digital script, including dynamic data and/or static data, a storage medium for storing information relating to the digital script, and instructions executable by the processor. When executed, the instructions may cause the processor to receive a secured digital script over the interface and extract selected portions of the dynamic data and/or the static data from the secured digital script. In certain embodiments, the instructions for extracting the selected portions include instructions for decoding and/or decrypting the secured digital script. In certain embodiments, the selected portions are selected by a designated branded user. In certain embodiments, the system further comprises instructions executable by the processor that, when executed, cause the processor to store the selected portions of the extracted data. The selected portions may be stored in the storage medium or in a network database.

The invention also relates to a method for generating, managing, and sharing digital scripts in an electronic prescription system. In certain embodiments, the method comprises the steps of selecting data relating to a digital script, including dynamic data and/or static data, merging selected portions of the dynamic data and/or the static data to create a digital script, and applying a security procedure to the digital script to create a secured digital script. The security procedure may include encoding and/or encrypting the digital script. In certain embodiments, the method may comprise outputting the secured digital script to a designated branded user or a storage device. The method may further comprise storing the secured digital script in the storage medium.

In certain embodiments, the method may comprise requesting the dynamic data and/or the static data from a network database over an interface for communicating with the network database in a computer network. The method may further comprise outputting the secured digital script to a network database over an interface for communicating with the network database in a computer network.

In certain embodiments, the method comprises receiving a secured digital script over an interface for communicating with a computer network, the secured digital script including dynamic data and/or static data, and extracting selected portions of the dynamic data and/or the static data from the secured digital script. In certain embodiments, the step of extracting the selected portions includes decoding and/or decrypting the secured digital script. In certain embodiments, the selected portions are selected by a designated branded user. In certain embodiments, the method further comprises storing the selected portions of the extracted data in the storage medium or in a network database.

The details of one or more embodiments of the present invention are set forth in the accompanying drawings and the description below. Other features, objects, and advantages of the present invention will be apparent from the description and drawings, and from the claims.

BRIEF DESCRIPTION OF THE DRAWINGS

FIG. 2 is a schematic diagram illustrating a system for generating, managing, and sharing digital scripts in accordance with some embodiments of the present invention;

FIG. 8 is a flow diagram illustrating modification and/or termination of a digital script in accordance with some embodiments of the present invention;

DETAILED DESCRIPTION

Overview

Figure 1:
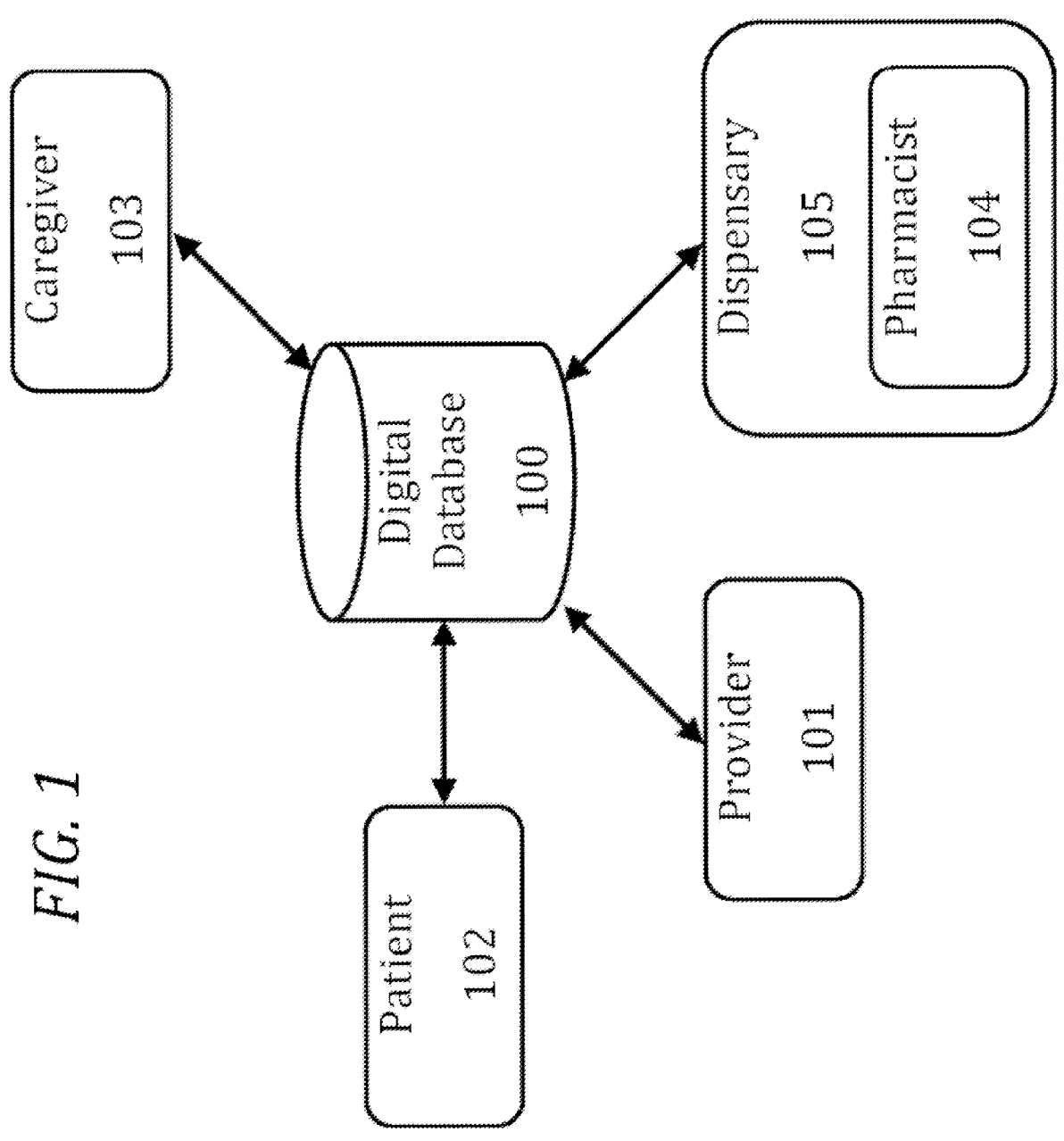
FIG. 1 is a network diagram illustrating a system for generating, managing, and sharing digital scripts in accordance with some embodiments of the present invention.

Embodiments of the present invention include new systems and methods for generating, managing, and releasing digital scripts. A digital script is a digital embodiment of a request for a prescription made by a health care provider. A digital script has the same validity for obtaining a prescription as traditional paper scripts or CPOE-generated facsimiles. The authority of a provider to generate a digital script may depend on local law and practice, especially with respect to a digital script requesting a controlled substance or device.

Embodiments of the present invention also include new systems and methods for accessing and sharing digital scripts. For example, in some embodiments, a patient may review a digital script, share prescription history with another provider, and/or obtain a prescription. The system only allows a patient access to digital scripts and information associated with his or her care (i.e., a "closed" access system at least with respect to the patient). However, other users (e.g., a provider or caregiver) may access multiple digital scripts, perhaps even from multiple providers, for multiple patients (i.e., an "open" access system).

A prescription is an actual medication or treatment, in its various forms, requested via a script and, as a result, obtained from an appropriate dispensary. Prescriptions may include instructions to be performed by a patient, caregiver, pharmacist, or other health care provider (e.g., behavioral counseling, physical therapy, and nutritional counseling). Prescriptions may also include a substance or device intended for use in medical diagnosis, cure, treatment or prevention of disease, such as medications (e.g., pills and creams), durable medical equipment (e.g., crutches and braces), implantable medical equipment (e.g., pacemakers and grafts), remote medical monitoring devices (e.g., wireless or wired sugar/hormone level monitors and blood pressure monitors), and over-the-counter health products (e.g., vitamins and prophylactics). Prescription medications, in particular, may be classified by chemical composition, route of administration, targeted biological system, or intended therapeutic effects. Prescriptions may further include clinical assessments, laboratory tests (e.g., blood work and tissue analysis), and diagnostic studies (e.g., x-ray and magnetic resonance imaging) related to a course of treatment or prevention of disease.

Embodiments of the present invention further include new systems and methods for a dispensary to receive, modify, and report digital scripts. A dispensary is an entity that "fills" a digital script by providing a patient with the prescription, if available and appropriate, requested in the script. An appropriately licensed pharmacy is a dispensary; however, a dispensary need not be limited to a pharmacy. Dispensaries may also include health care facilities, retail stores, Internet or mail order companies, and rental distributors. Upon production of a valid digital script at a dispensary, an appropriate individual (e.g., a licensed pharmacist) employed by the dispensary processes the digital script and dispenses the prescription, if available and appropriate, requested in the script.

User Branding

In accordance with some embodiments of the present invention, the actions available to a particular user with respect to a particular digital script depend on how that user has been "branded" within the system. Each branded user accesses the system and interacts with a digital script according to a previously-bestowed designation as, for example, a branded provider, a branded pharmacist, a branded patient, and/or a branded caregiver.

FIG. 1 shows a network diagram in accordance with some embodiments of the present invention. The network diagram of FIG. 1 includes a digital database 100 and four types of users: a branded provider 101, a branded patient 102, a branded caregiver 103, and a branded pharmacist 104. The branded pharmacist 104 is associated with a dispensary 105. Each branded user has access to user equipment (e.g., a mobile device, tablet, or computer) and may communicate with the digital database 100 and/or another branded user across one or more communication networks, as discussed in greater detail below.

A branded provider is a user who has been designated in the system to generate a digital script on behalf of a patient in accordance with some embodiments of the present invention. The authority to generate a digital script, especially with respect to a script requesting a controlled substance or device, may depend on local law and practice. A branded provider may be a physician, physician assistant, nurse practitioner, advanced practice nurse, dentist, veterinarian, clinical pharmacist, optometrist, psychiatrist, medical psychologist, chiropractor, etc. In some embodiments of the present invention, a digital script is labeled with the identity of the branded provider who generated it. This label may be based upon a National Provider Identification (NPI) number assigned by the American Medical Association (AMA) or a U.S. Drug Enforcement Administration (DEA) number. In further embodiments of the present invention, a branded provider may modify, renew, terminate, and/or share digital scripts within the system. In certain embodiments of the present invention, a digital script may include a referral, by which a branded provider refers a patient to another provider, who may be branded.

A branded pharmacist is a user who has been designated in the system to dispense a prescription (e.g., medication, medical goods, equipment, or services) as directed by a valid digital script to a patient in accordance with some embodiments of the present invention. The authority to dispense a prescription, especially a controlled substance or device, may depend on local law and practice. In some embodiments of the present invention, a digital script is labeled with the identity of the branded pharmacist who filled it. This label may be based upon a Pharmacist's Representative Number (PRN) and/or an Individual Dispensary Location (IDL) number. In further embodiments of the present inventions, a branded pharmacist may modify a digital script by, for example, reducing the number of remaining refills associated with the digital script. Depending on local law and practice, a branded pharmacist may modify a digital script that requests a brand version of a medication in order to dispense a generic version of the medication (and/or vice versa) in accordance with some embodiments of the present invention. In additional embodiments, a pharmacist may accept health insurance information and/or electronic payments for prescriptions via the same system.

A branded patient is a user who has been designated in the system to obtain a prescription as directed by a valid digital script in accordance with some embodiments of the present invention. The type of healthcare sought by a patient may include medical, dental, surgical, or other treatment. In some embodiments of the present invention, a digital script is labeled with the identity of the branded patient on whose behalf it was generated. This label may be based upon a Social Security Number (SSN) or unique Medical Record Number (MRN). In further embodiments of the present invention, a digital script is labeled with a diagnosis code. A diagnosis code may be obtained from, for example, the World Health Organization's International Statistical Classification of Diseases and Related Health Problems (ICD), particularly the ICD-9 and ICD-10 code sets.

A branded caregiver is a user who has been designated in the system as an administrator of care for a branded patient in accordance with some embodiments of the present invention. Non-limiting examples of patients who may voluntarily designate branded caregivers, or have branded caregivers designated on their behalf, include minors, seniors, disabled persons, and animals. The authority to administer care on behalf of a patient, especially to obtain and administer a controlled substance or device, may depend on local law and practice. For example, a caregiver may be authorized by a court if a patient is deemed unfit to manage his or her own care. Alternatively, a branded patient may voluntarily designate a branded caregiver. In some embodiments of the present invention, a digital script is labeled with the identity of a branded caregiver who obtained the prescription on behalf of a patient. This label may be based upon an SSN or another unique identifier.

Digital Script Generation and Management

Embodiments of a digital script are digital representations of a request for a prescription made by a health care provider. A digital script has the same information and validity as a traditional paper script or a CPOE-generated facsimile script, except that a digital script is encoded and maintained in an electronic format in accordance with some embodiments of the present invention.

In some embodiments, a digital script is encoded and shared as a barcode image. Many dispensaries already utilize barcode-based systems, wherein products are marked with one-dimensional (1-D) or two-dimensional (2-D) barcode images, for inventory tracking and checkout efficiency. Likewise, most providers and patients have access to hardware and software capable of generating and/or reading barcodes. Barcode images may be shared via an electronic visual display (e.g., a mobile device screen or a checkout monitor), printed on paper (e.g., by a kiosk or checkout receipt printer), or transmitted over a communication network (e.g., the Internet or a cellular network). Barcode images may be read using a camera or scanner and a decoder that analyzes the image data provided by the camera or scanner. For example, most mobile devices comprise cameras that are capable of reading barcode images, especially 2-D barcodes that have been optimized for cellular phone cameras and other cameras without auto-focus capabilities.

In preferred embodiments, a digital script is encoded and shared as an optimized 2-D barcode, such as a 2-D Quick Response (QR) Code, a micro QR Code, a Data Matrix, a PDF417 barcode, or a micro PDF417 barcode. Compared to linear barcodes, QR Codes, for example, have larger volume data capacity and achieve high-speed, 360-degree reading with or without an auto-focus camera. In addition, QR Codes offer high-density recording with language-based efficiencies, linking functionality, easy encryption, and resistance to symbol distortion, smudges, and damage. An international standard defining the requirements for QR Codes is ISO/IEC18004:2006, which is incorporated herein in its entirety.

In some embodiments, a digital script is encoded and shared as any optical machine-readable representation of data (e.g., using optical character recognition or an optical disc or tape). In other embodiments, a digital script is encoded and shared using character-encoding schemes, such as ASCII or Unicode. In still further embodiments, a digital script is encoded and shared using magnetic media (e.g., a magnetic disk, tape, ink, or strip), semiconductors, floating-gate transistors (e.g., flash memory), or radio transmission (e.g., a radio frequency identification (RFID) tag, a near-field communication (NFC) tag, or Bluetooth technology).

By generating a digital script with encoded fields (e.g., patient identity and number of refills remaining), a branded provider enables a branded patient and/or branded caregiver to efficiently obtain a prescription while maintaining a digital record and, if refills are available, a digital script for the unfilled balance. In some embodiments, a digital script evolves with use. That is, the system may automatically update a field based on an event or otherwise allow a field to be modified by an authorized branded user. A field in an evolving digital script that may be updated or modified is a dynamic field. In further embodiments, the system may include a dynamic network database or other data structure that automatically receives and updates information regarding digital scripts in the network; and each digital script, when it is decoded, contains a digital link (e.g., a Uniform Resource Locator (URL)) to the database.

For example, in some embodiments, if a branded pharmacist dispenses a prescription associated with a digital script, the system may automatically update a dynamic field of the evolving digital script to show that the digital script has been filled. In addition, if a digital script provides for refills, the system may automatically update a dynamic field representing the number of refills remaining by deducting one for each refill obtained by the patient or caregiver. Alternatively, a branded pharmacist may manually modify a dynamic field of a digital script to show that the digital script has been filled, to identify the branded pharmacist who filled the digital script, and/or deduct from the number of remaining refills. Likewise, in some embodiments, a branded provider may take actions that automatically update or manually modify a digital script, such as increasing the number of remaining refills to renew a digital script or canceling the number of remaining refills to terminate a digital script.

According to some embodiments, following generation of a digital script, the system may maintain static fields, which may not be modified by any branded user. For example, the static fields of a digital script may include the identity of the branded provider who generated the digital script and/or the identity of the branded patient on whose behalf it was generated. A field that may only be modified by one type of branded user is dynamic to that branded user, but may be static to all other types of branded users. Similarly, a field that may only be modified by one specific branded user is dynamic to that branded user, but may be static to all other branded users.

In some embodiments, events or modifications by an authorized branded user may cause the system to change a dynamic field to a static field. For example, in accordance with some embodiments, once the system updates or modifies a dynamic field of a digital script to identify a branded pharmacist who filled the digital script, that dynamic field may become a static field so that the identity of the branded pharmacist is maintained in a history of the evolving digital script.

In accordance with some embodiments of the present invention, a digital database or other data structure may be utilized to maintain digital scripts as well as other patient healthcare records. A digital database may be implemented using a proprietary or open-source database platform. In preferred embodiments, the digital database is a dynamic, online database that is accessible from a network (e.g., the Internet). Some embodiments may utilize a web-based database management system, including, for example, MySQL™ (Oracle Corp., Redwood Shores, Calif.), SQL Server® (Microsoft Corp., Redmond, Wash.), or DB2C, (IBM Corp., Armonk, N.Y.). In alternative embodiments of the present invention, digital scripts and records may be stored and organized in a data structure other than a database, such as a distributed hash table, or in a hybrid data structure that shares some properties of a database, such as DynamoDB (Amazon Web Services, Inc., Seattle, Wash.).

In some embodiments, the digital database or other data structure is a cloud-based repository. The cloud infrastructure and services may be managed and/or hosted using one or a hybrid of the following deployment models: private, community, or public. A cloud service provider—like Amazon Web Services, Inc. (Seattle, Wash.), Windows Azure™ Cloud Services (Microsoft Corp., Redmond, Wash.), Google Cloud Platform (Google, Inc., Mountain View, Calif.), or Rackspace® (San Antonio, Tex.)—may be used to access cloud infrastructure and services.

In accordance with some embodiments of the present invention, the digital database or other data structure is hosted on a server with network (e.g., Internet) access, thus making digital scripts and records available to multiple branded users on different UE devices. The server may be owned or leased for use from a network (e.g., Internet or cloud) hosting service. The server may actually consist of one or more servers utilizing one or more server protocols.

The server may be a database server or a server that provides database services as well as other services, for example, connecting HTTP clients in order to send commands and receive responses and/or data (i.e., a web server).

Some embodiments of the present invention are designed to meet local regulations governing the exchange of personal and/or health information. In preferred embodiments, the digital database or other data structure meets the standards proposed under the U.S. Health Insurance Portability and Accountability Act (HIPAA) for all information transmitted to, from, and between branded users in the system. In further embodiments, the systems are automatically updated to meet regulatory changes, such as revisions to HIPAA.

A digital database or other data structure may maintain a history of the evolving digital script, including an access log. In some embodiments, a branded user may even customize an alert service (e.g., via email, short messaging service (SMS), and push notification) to notify the user of updates (e.g., to a digital script) in the digital database or other data structure, according to predefined alert preferences.

In some embodiments, a branded user may access and interact with a digital database or other data structure over a prescription management software application using an interface, such as a Graphical User Interface (GUI). A branded user may list or select preferences. For example, branded patient 102 may list or select a primary care provider (e.g., branded provider 101), a preferred dispensary (e.g., dispensary 105), and an authorized caregiver (e.g., branded caregiver 103). Branded patient 102 may also disclose known health issues, such as allergies (e.g., to food and medications), treatment complications (e.g., hemophilia), and chronic conditions (e.g., diabetes). Branded patient 102 may even upload and store insurance or payment information. All of these patient healthcare records may be stored in a digital database and be accessed by authorized branded users via a prescription management application.

In accordance with some embodiments of the present invention, a prescription management software application is hosted on a server with network (e.g., Internet) access, thus making digital scripts and records available to multiple branded users on different UE devices. The server may be owned or leased for use from a network (e.g., Internet or cloud) hosting service. The server may actually consist of one or more servers utilizing one or more server protocols. The server may be a web server or a server that provides web services as well as other services (e.g., a database server). Digital Script Security and Privacy In some embodiments of the present invention, a digital script may be encrypted to prevent all but authorized branded users to decode the script. Likewise, access to a centralized digital database may be restricted. Various encryption and authentication schemes may be implemented in order to maintain system security and preserve the integrity and privacy of the information encoded in each digital script. For example, these schemes may include symmetric-key cryptography algorithms, public-key cryptography algorithms, or some hybrid cryptosystem.

In some embodiments, the cryptography algorithm is a cipher, such as the data encryption standard, triple-data encryption standard, or the advanced encryption standard. In a preferred embodiment, a fixed length string of plaintext bits of a block size of, for example, 64 bits, or multiples thereof (e.g., 128 bits or 256 bits), is encrypted to yield a string of bits of equal size. The block size can be any power of two to yield an encrypted string of bits of equal size. The algorithm utilizes a uniquely generated 64-bit key (or, e.g., 128-bit key, 256-bit key, etc.), which is used to generate a number of sub-keys through a series of shifts of the hexadecimal numbers using defined lengths of shifts. The plaintext bits are initially subject to a permutation where the location of each bit in the string is modified. The modified string is then divided into two equally-sized halves. The algorithm combines the first half of the string with a specific sub-key then subjects it to non-linear transformations through substitutions from a pre-determined data table. After each non-linear transformation, the transformed half of the string is combined with the second half of the string. The recombined 64-bit string undergoes another permutation followed again by division into two equally-sized halves. The same process as described above is repeated using a different sub-key. The number of sub-keys determines the number of processing stages, and the number of processing stages determines the strength of the encryption. After the processing stages are completed, the recombined 64-bit string undergoes inversion to the initial permutation, thus finalizing the encryption process. As long as the original 64-bit key is known, the above algorithm is reversible and the data may be decrypted.

Due to the sensitive nature of healthcare information, access control is important in all embodiments of the present invention. For example, in certain embodiments, one or more third parties (e.g., a certificate authority) may be defined to issue and verify identity certificates, such as Public Key Infrastructure (PKI) digital certificates, to all of the branded users associated with a digital script. Each identity certificate is unique and uses a digital signature to bind a public key with a branded user. A third party authenticates the identity of each branded user by binding its own certificates to public keys for verifiable certificate chains.

In accordance with some embodiments of the present invention, the different types of branded users shown in FIG. 1 define different access requirements with respect to a digital script. For example, following the generation of the digital script by a branded provider 101, each authorized branded user may apply a digital signature to the evolving digital script, which is recorded and updated in a digital database 100. In a specific embodiment, a branded provider 101 may automatically record the creation of a digital script by simply transmitting the script with a digital signature across a communication network to the digital database 100 and/or directly to a branded patient 102 or a branded caregiver 103.

Branded patients 102 and caregivers 103 are permitted only to view and share digital scripts according to some embodiments. However, like a branded provider, a branded patient 102 or caregiver 103 may automatically record access to a digital script by simply viewing the script with a digital signature over a communication network. Alternatively, a branded patient 102 or caregiver 103 may automatically record access to a digital script by simply transmitting the script with a digital signature across a communication network to the digital database 100 and/or directly to a branded pharmacist 104 at a dispensary 105.

After dispensing a prescription, a branded pharmacist 104 may record partial or complete filling of a digital script by transmitting the script with a digital signature from its point-of-sale terminal across a communication network to the digital database 100. For each event, a third party may authenticate the identity of the branded user and—if the evolving digital script is valid—add the record to the patient's digital script access log and prescription history in the digital database 100.

Further embodiments of the system work to exclude unauthorized users by requiring branded users to supply one or more of the following credentials: personal knowledge (e.g., a password, Personal Identification Number (PIN), or CAPTCHA phrase), physical objects (e.g., an access card or mobile device), and biometric features (e.g., dactylscopy, retinal scan, or voice recognition).

Implementations of a Digital Script-Based System

Embodiments of the present invention may be implemented in various forms of hardware, software, firmware, or a combination thereof. In some embodiments, modules are implemented in software as application programs that are then executed by user equipment (UE). The UE may include a mobile phone, a laptop with wireless connectivity, a netbook, a smartphone, or any other wireless device. The UE also may encompass many other devices such as televisions (TVs), video projectors, set-top boxes or set-top units, digital video recorders (DVR), computers, netbooks, laptops, and any other audio/visual equipment that can communicate with a network.

Figure 2:
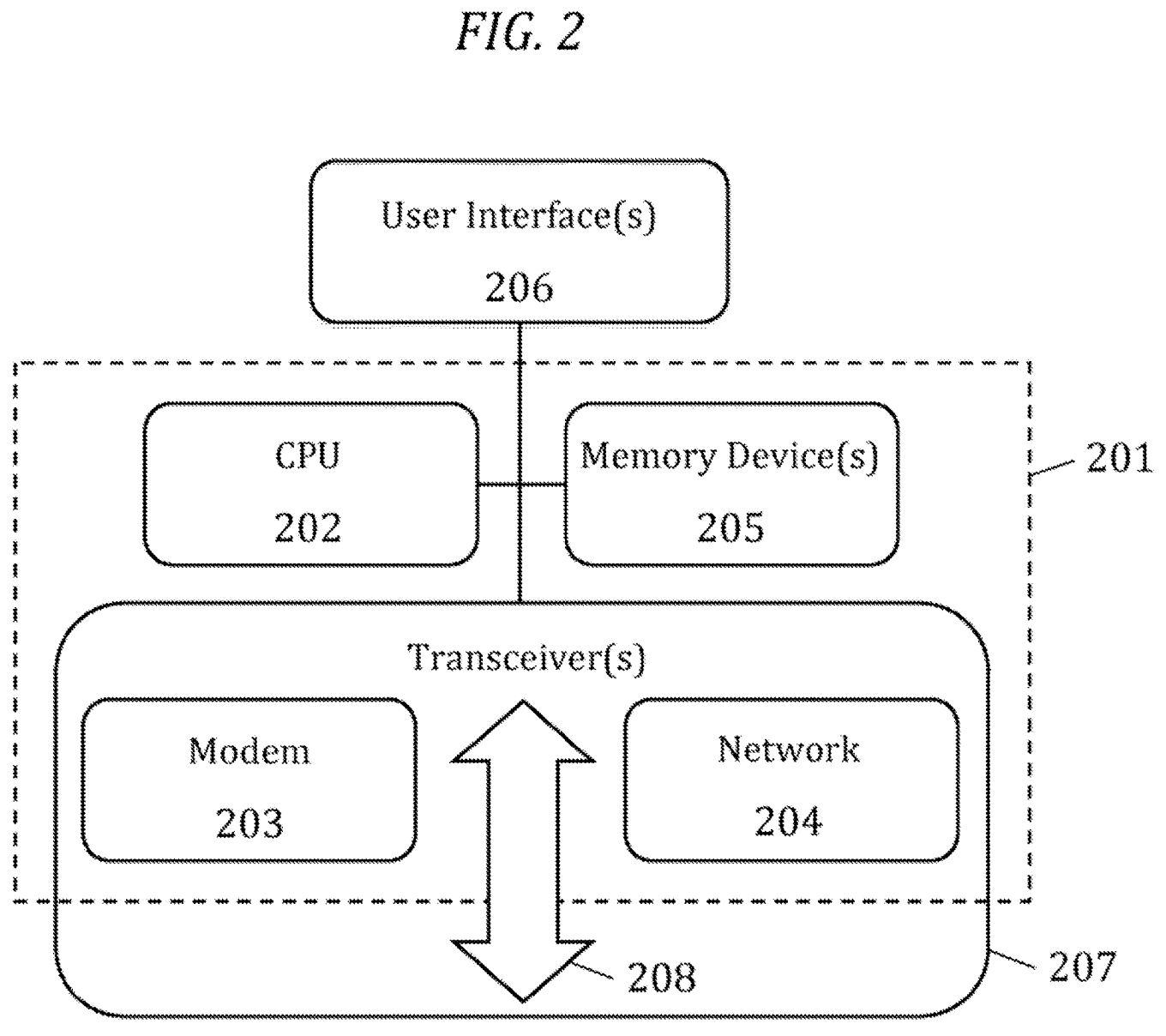

FIG. 2 illustrates a schematic view of UE 201 for generating, modifying, and sharing digital scripts in accordance with certain embodiments. The UE 201 may include a central processing unit (CPU) 202, a modem 203, a network interface selection module 204, one or more memory devices 205, one or more user interfaces 206, and one or more transceivers 207 with interfaces 208.

The CPU 202 executes processes performed by the UE 201. The UE can be configured with one or more processors that process instructions and run software that may be stored in memory. In some embodiments, the software needed for implementing a process or a database includes a high level procedural or an object-orientated language such as C, C++, C#, Java, or Perl. The software may also be implemented in assembly language if desired. Packet processing implemented in a UE can include any processing determined by the context. For example, packet processing may involve high-level data link control (HDLC) framing, header compression, and/or encryption. The processor can be any applicable processor that combines a CPU, an application processor, and memory. Applicable processors can include any microprocessor (single or multiple core), system on chip (SoC), microcontroller, digital signal processor (DSP), graphics processing unit (GPU), combined hardware and software logic, or any other integrated circuit capable of processing instructions.

In certain non-limiting embodiments, the processes performed by the UE 201 may include encoding to create or modify a digital script, encrypting to secure a digital script, decoding/decrypting to access a digital script, verifying a branded user's identity/permissions, and performing transactions to obtain/dispense a prescription.

The modem 203 is configured to implement modulation and framing of signals according to one or more communication standards including, but not limited to, WLAN-related standards, such as 802.11 (e.g., 802.11a, 802.11b, and/or 802.11g), and the cellular standards, such as those defined under 3GPP and 3GPP2.

The UE 201 can communicate with a plurality of radio access networks using a plurality of access technologies as well as with wired communication networks. The network interface selection module 204 selects a network interface from which to receive network services. The network interface selection module 204 may interface with different types of communication networks, including, but not limited to, cellular networks (e.g., 2G, 3G, 4G, and LTE) and WLANs. In some embodiments, the network interface selection module 204 selects a network interface by analyzing data load information associated with available interfaces. In certain embodiments, the network interface selection module 204 may be configured to attach to a network interface handling the least amount of data traffic and/or with more available resources. In further embodiments, the network interface selection module 204 also analyzes additional information to decide to which network interface to connect. The network interface selection module 204 may be implemented in hardware using an application specific integrated circuit (ASIC), programmable logic array (PLA), or any other integrated circuit. The network interface selection module 204 may also be implemented in software using the memory device 205.

The UE has one or more memory devices 205 such as a non-transitory computer readable medium, flash memory, a magnetic disk drive, an optical drive, a programmable read-only memory (PROM), and/or a read-only memory (ROM). The one or more memory devices 205 may also store the instructions for the above processes, which are executed by the CPU 202. The one or more memory devices 205 may store a branded user's information, including static data and/or dynamic data input by the user.

The one or more user interfaces 206 provide input and/or output mechanisms to communicate with UE users. UE users send/receive digital scripts to/from the UE 201 through the one or more user interfaces 106. The one or more user interfaces 206 can be implemented in hardware or software. The one or more user interfaces 206 can be used to receive both data and control information from the network as well as local sources. Input devices for secure digital scripts may include, but are not limited to, a barcode reader, an image scanner, and a camera. Meanwhile, output devices for transmitting and/or sharing digital scripts include, but are not limited to, a screen, a touch screen, a monitor, and a printer. Other input/output devices may include, but are not limited to, the modem 203, a transceiver 207 with interfaces 208, a keyboard, a microphone, a speaker, a pen device, a trackball, a touch pad, and a mouse. The one or more user interfaces 206 can operate under a number of different protocols. In some embodiments the one or more user interfaces 206 are implemented through software, and in other embodiments, the one or more user interfaces 206 are implemented in hardware to send and receive signals via transceiver 207 in a variety of mediums, such as optical, copper, and wireless.

The one or more transceivers 207 each include a transmitter and a receiver. The transmitter and the receiver may be integrated into a single chip or may be embodied in separate chips, or may even be integrated with the CPU 202 and/or one or more memory devices 205. In some embodiments, the one or more transceivers 207 include interfaces, shown collectively as interface 208, that provide an input and/or output mechanism to communicate with other network devices (e.g., UE operated by other branded users). In some embodiments, the interface 208 measures and outputs the wireless signal strength of wireless interfaces, such as base stations and access points. The interface 208 may be implemented in hardware to send and receive signals in a variety of mediums, including, but not limited to, optical wires, copper wires, and wireless, and in a number of different protocols some of which may be non-transient.

In some embodiments, the UE is a smart phone offering advanced capabilities such as word processing, web browsing, gaming, e-book capabilities, an operating system, and a full keyboard. The UE may run an operating system such as Symbian OS, Apple iOS, Blackberry OS, Windows Mobile, Linux, Palm WebOS, and Android. The screen may be a touch screen that can be used to input data to the UE that can be used instead of the full keyboard. A microphone and voice recognition software may also be used to input data to the UE. The UE may have the capability to run applications or communicate with applications that are provided by servers in the communication network. The UE may receive updates and other information from these applications on the network. The UE may also keep global positioning coordinates or other location information in its stack or memory.

While the systems and methods have been described above primarily in conjunction with mobile devices, the generation, management, and sharing of digital scripts could also be performed with stationary devices and over fixed broadband, such as a personal desktop computer, computer kiosk, or a point-of-sale terminal being used over a wired network (or wire in conjunction with wireless, such as WLAN). In the case of a WLAN system, the user station would communicate to an access point that would then be in communication via the Internet with other entities, as is generally known.

Examples of Using a Digital Script-Based System

Figure 3:
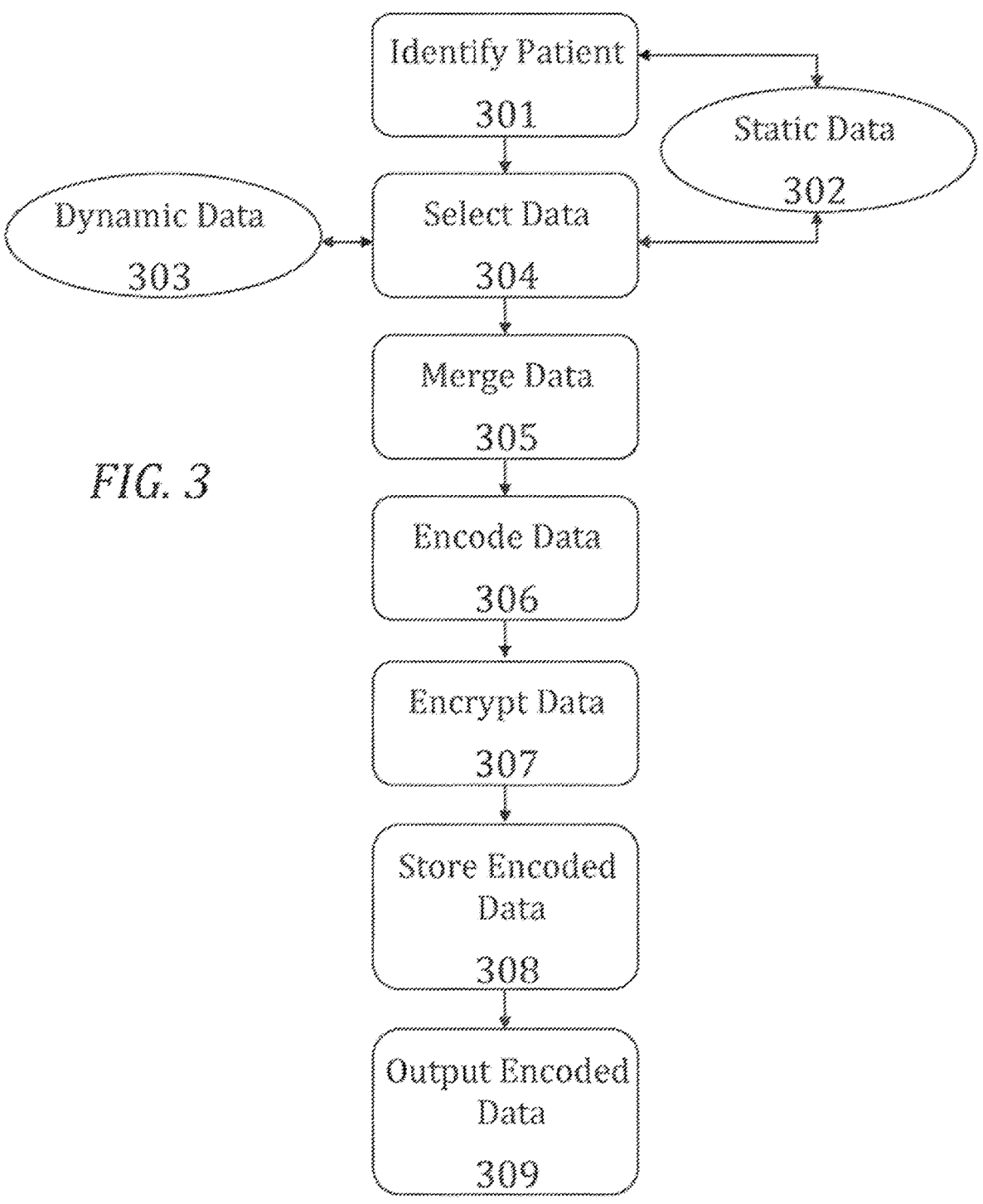
FIG. 3 is a flow diagram illustrating a system for generating, managing, and sharing digital scripts from the perspective of a branded provider in accordance with some embodiments of the present invention.

FIG. 3 depicts a flow diagram of a system for generating, managing, and sharing digital scripts from the perspective of a branded provider in accordance with some embodiments of the present invention. In order to generate a digital script for a branded patient, a branded provider identifies the patient in step 301 and retrieves static data 302 associated with the patient. Static data 302 may include, but is not limited to, prescription data, an order set, prescription interaction data, a customized medical directive, a diagnosis code, patient data, caregiver data, provider data, pharmacist data, dispensary data, data extracted from an existing digital script, insurance data, payment data, a record of generating a new digital script, a modification to an existing digital script, a record of filling a digital script, and a representation of the number of refills remaining.

An order set is a predetermined series of prescriptions that a branded provider prescribes for a particular treatment. A customized medical directive associated with the prescription may be tailored to a specific branded patient. A diagnosis code may be provider-specified or obtained from, for example, the ICD code sets. Patient data may include identification of the branded patient, such as an SSN or unique MRN, as well as contact and treatment information. Caregiver data may include identification of the branded caregiver, such as an SSN or another unique identifier, as well as contact and relationship information. Provider data may include identification of the branded provider, such as an NPI and/or DEA number, as well as contact and practice information. Pharmacist and/or dispensary data may include identification of the branded pharmacist and/or dispensary, such as a PRN and/or IDL number, as well as contact information.

Next, the branded provider selects static data 302 and/or dynamic data 303 in step 304. Dynamic data 303 may include, but is not limited to, prescription data, an order set, prescription interaction data, a customized medical directive, a diagnosis code, patient data, caregiver data, provider data, pharmacist data, dispensary data, data extracted from an existing digital script, insurance data, payment data, a record of generating a new digital script, a modification to an existing digital script, a record of filling a digital script, and a representation of the number of refills remaining.

In step 305, the selected static data 302 and/or dynamic data 303 are merged to generate a new digital script or modify an existing digital script. The digital script is encoded into a machine-readable representation, such as a QR Code in step 306. The encoded digital script may be encrypted in step 307 using one or more encryption algorithms to control access to the underlying information, thus preserving the privacy and integrity of the digital script during transmissions between authorized branded users.

In step 309, the branded provider shares a digital script following encoding and/or encryption by outputting the digital script by, for example, transmitting the digital script directly to another branded user. In other examples, the branded provider may store the digital script (either before output as in step 308, after output, or instead of output), for instance, by saving the digital script into a local memory device or a centralized digital database, which is selectively accessible to the branded patient, any branded caregiver, and any branded pharmacist with authorization. Embodiments using a common digital database may allow for monitoring/recording of user access and a real-time history of an evolving digital script.

Figure 4:
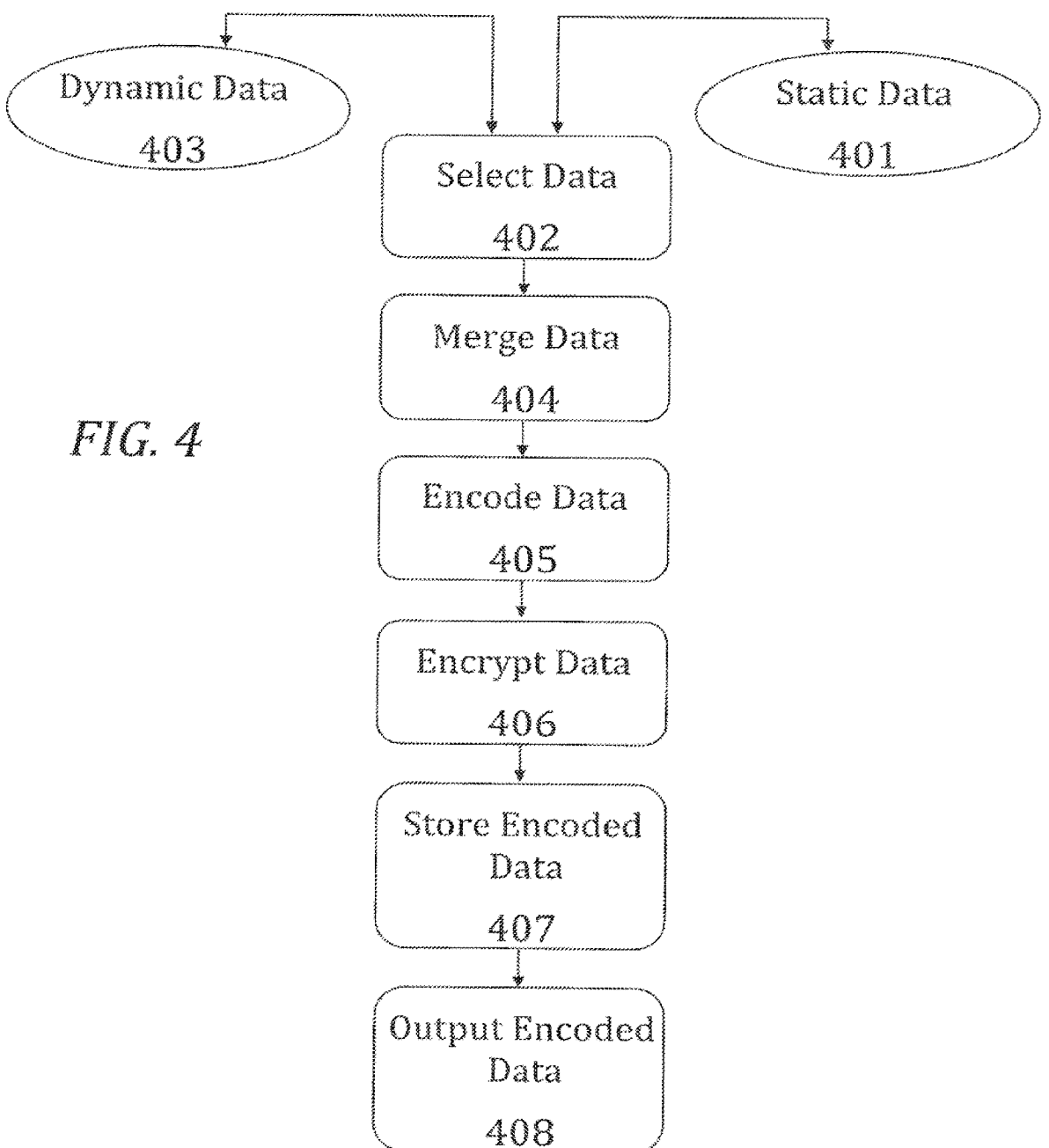
FIG. 4 is a flow diagram illustrating a system for generating, managing, and sharing digital scripts from the perspective of a branded patient in accordance with some embodiments of the present invention.

FIG. 4 depicts a flow diagram of a network for generating, managing, and sharing digital scripts from the perspective of a branded patient in accordance with some embodiments of the present invention. A branded patient either receives a digital script directly from a branded provider or retrieves a stored digital script from a common digital database. Because a branded patient is permitted to only access and not modify a digital script, the script is a type of static data 401.

In certain embodiments, a branded patient may select additional data to add to the digital script as in step 402. This data may include other static data 401, such as insurance or payment information, and/or dynamic data 403, such as the amount of refills requested or information pertaining to discounts, coupons, or reward programs. In some embodiments, a branded patient can select among insurance options and/or a set of stored payment options including, but not limited to, credit cards, debit cards, Health Savings Accounts, Federal Savings Accounts, checking accounts, savings accounts, PayPal®, or any other remittance accounts that electronically process payments. In further embodiments, the payment options may also allow for coupons, discounts, and reward programs.

Then, static data 401 and/or dynamic data 403 are merged in step 404 to expand an existing digital script. In step 405, the evolving digital script is encoded into a machine-readable representation. The encoded digital script may be encrypted in step 406 to limit access and/or modification permissions to only specific branded users.

According to further embodiments, a branded patient shares an evolving digital script following encoding and/or encryption by outputting the evolving digital script in step 408. The output step 408 may involve transmitting the digital script directly to another branded user. In other embodiments, the branded patient may store the digital script (either before output as in step 407, after output, or instead of output), for instance, by saving the digital script into a local memory device or by copying the digital script from a local memory device to a common digital database, which may be accessible by a branded pharmacist with the patient's permission.

Embodiments that utilize a common digital database may monitor user access and record a real-time history of digital script access available to branded users with permission to view. These or other embodiments may also allow for a specific branded user to be notified of new or updated digital scripts through any appropriate communication means (e.g., email, short messaging service (SMS), and push notification).

In an exemplary embodiment, a branded patient uses this process to create a Request For Prescription (RFP), which is a request for a refill of a prescription that has been previously dispensed to the patient according to a digital script. In preferred embodiments, a branded patient can use this process to fill two or more digital scripts at the same time. However, an alert or another action can be taken if the two or more prescriptions associated with the digital scripts present a risk of undesirable or hazardous interaction.

Figure 5:
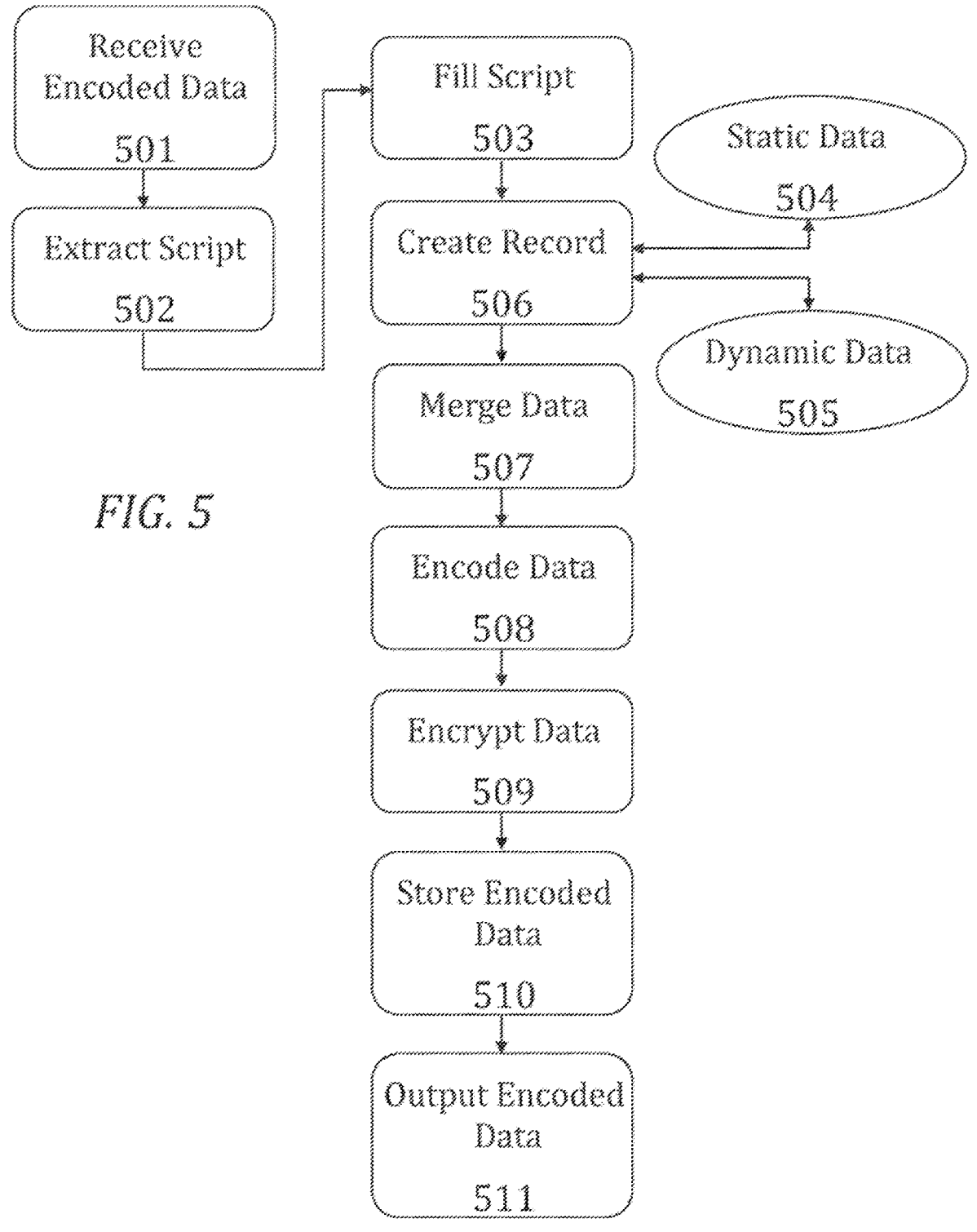
FIG. 5 is a flow diagram illustrating a system for generating, managing, and sharing digital scripts from the perspective of a branded pharmacist in accordance with some embodiments of the present invention.

FIG. 5 is a flow diagram of a network for generating, managing, and sharing digital scripts from the perspective of a branded pharmacist in accordance with some embodiments of the present invention. In step 501, a branded pharmacist either retrieves a digital script from a common digital database or receives a digital script directly from a branded patient, provider, or caregiver. The branded pharmacist decrypts and decodes the digital script in order to extract the information that is necessary to dispense a prescription in step 502. This information may include, but is not limited to, the original digital script as well as insurance information, payment information, and any other static and/or dynamic data provided by the user. Once a branded pharmacist is able to access and view the necessary information, the branded pharmacist fills the digital script in step 503 by dispensing the prescription to the branded patient and/or branded caregiver.

In certain embodiments, step 502 or step 503 itself, or an aspect thereof, is recorded as part of the evolving digital script by adding a field to or completing an existing field in the script with the branded pharmacist's PRN. Because a branded pharmacist is permitted to modify only particular fields associated with an evolving digital script, the remaining fields of the digital script may be considered static data 504. In some embodiments, a branded pharmacist may select additional data to add to the digital script as in step 506. This data may include other static data 504, such as insurance or payment information, and/or dynamic data 505, such as the amount of remaining refills, record of generic substitution for a brand prescription (or vice versa), or information pertaining to discounts, coupons, or reward programs.

Then, static data 504 and/or dynamic data 505 are merged in step 507 to expand an existing digital script. In step 508, the evolving digital script is encoded into a machine-readable representation. The encoded digital script may be encrypted in step 509 to limit access and/or modification permissions to only specific branded users.

According to further embodiments, a branded pharmacist shares an evolving digital script following encoding and/or encryption by outputting the evolving digital script in step 511. The output step 511 may involve transmitting the digital script directly to another branded user. In other embodiments, the branded patient and/or branded caregiver stores the digital script (either before output as in step 510, after output, or instead of output), for instance, by saving the digital script into a local memory device or by copying the digital script from a local memory device to a common digital database, which may be accessible by a branded pharmacist with the permission of the branded patient and/or branded caregiver.

Embodiments using a common digital database may monitor user access and make a real-time history of digital script access available to branded users with permission to view. These or other embodiments may also allow for a specific branded user to be notified of new or updated digital scripts through any appropriate communication means (e.g., email, short messaging service (SMS), and push notification).

In some embodiments, a user may register as a branded provider, branded pharmacist, branded patient, or branded caregiver. One user may access the network as multiple branded users; however, each user may only register once under some types of branding in some embodiments. For example, a provider may register both as a branded provider and as a branded patient, but cannot register as a branded patient again. However, in some embodiments, a provider may be allowed to register multiple times as a branded provider, each account representing a different (e.g., hospital versus private) practice.

Figure 6:
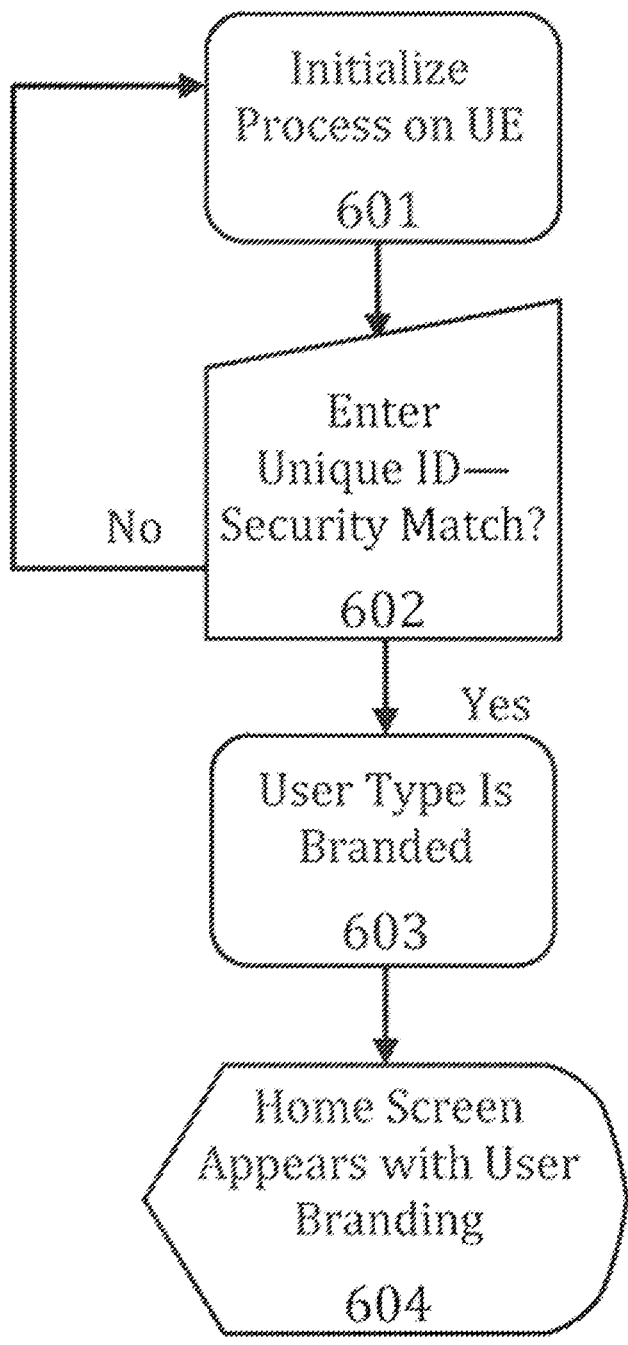
FIG. 6 is a flow diagram illustrating initialization and branding of a user in accordance with some embodiments of the present invention.

FIG. 6 is a flow diagram illustrating branding of a user in accordance with some embodiments of the present invention. In step 601, a user initializes the branding process by registering with or accessing the system on a UE, such as a tablet, smart phone, desktop computer, or portable computer, that has a network connection.

For security, a user may be required to choose a unique PIN during registration. Additional information may be collected in case the user forgets or needs to reset the PIN. A user may also be assigned a unique identification number (ID). In some embodiments, an ID comes from a random-number generator. In other embodiments, an ID is an existing identification number, such as a social security number, driver's license number, insurance policy number, or telephone number.

According to step 602, a user must enter the correct PIN and/or ID to access the network. If the PIN and/or ID match the records associated with a specific user, the user is branded in step 603 and granted a set of specific permissions relating to generation, access, modification, and sharing of digital scripts. In step 604, the network interface reflects the type of branding.

Figure 7:
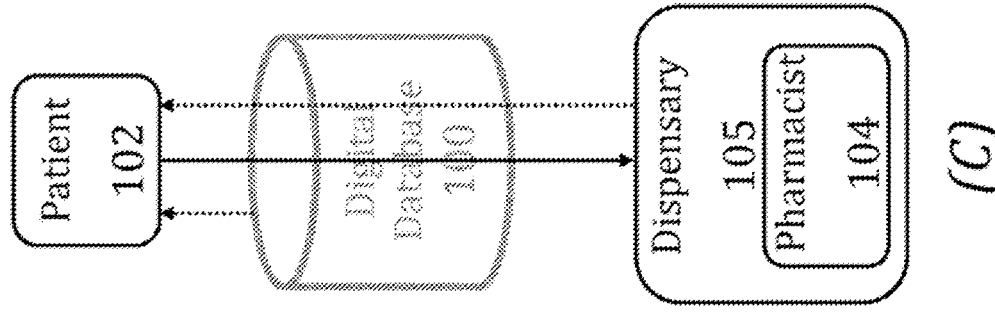
FIGS. 7A, 7B, and 7C are flow diagrams illustrating routing of a digital script between branded users in accordance with some embodiments of the present invention.
Figure 7:
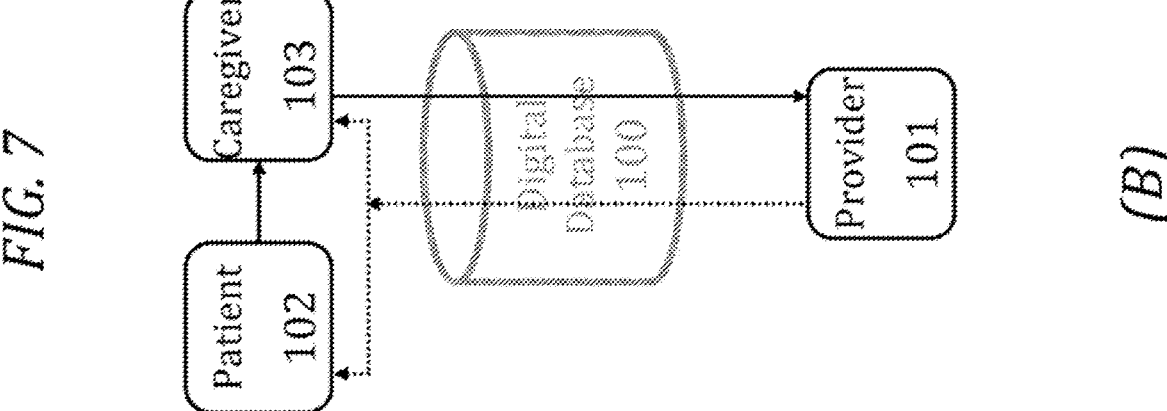
Figure 7:
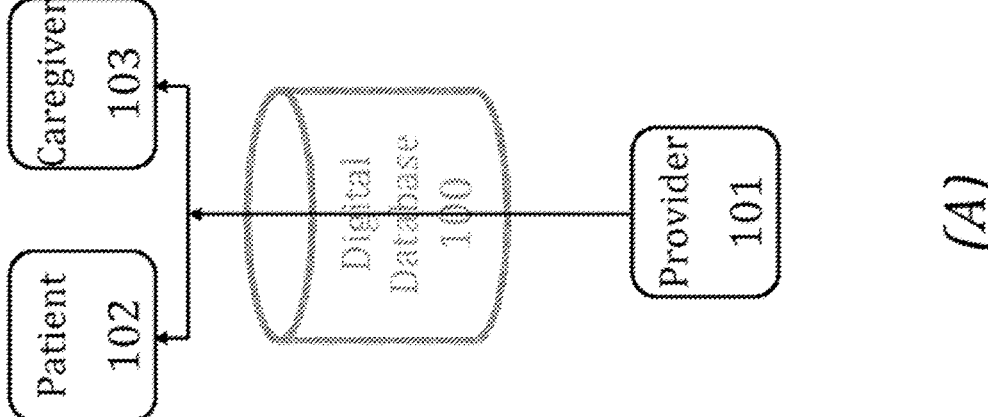

FIG. 7 is a collection of flow diagrams illustrating the routing of a digital script between branded users according to some embodiments of the present invention. FIG. 7 depicts exemplary use cases for the network depicted in FIG. 1. The diagram in FIG. 7(A) illustrates the flow of digital scripts from a provider 101 to a patient 102 as well as a caregiver 103 through digital database 100. A user interface with the digital database 100 permits a patient 102 and/or caregiver 103 to access and view changes to the patient's digital scripts.

The diagram in FIG. 7(B) illustrates a patient 102 approving a caregiver 103, who then requests a refill authorization from a provider 101. The diagram also shows the flow of the refill authorization, just as in (A), from the provider 101 to the patient 102 as well as the caregiver 103 through digital database 100. A user interface with the digital database 100 permits a patient 102 and/or caregiver 103 to access and view the refill authorization.

In preferred embodiments, a branded patient authorizes a branded caregiver by either inviting or accepting an invitation from the branded caregiver to link network profiles. A branded patient may also de-authorize a branded caregiver, in which case the branded caregiver can no longer access the branded patient's network profile. In some embodiments, previous caregivers are recorded as part of the branded patient's medical history.

The diagram in FIG. 7(C) illustrates the presentation of a digital script through digital database 100 in order to obtain a prescription. For example, a patient 102 may go to a dispensary 105 with the intent of using a digital script to obtain a prescription. The patient 102 uploads the digital script to digital database 100, and a pharmacist 104 retrieves the digital script. After the pharmacist fills the digital script by dispensing the prescription, the digital database is updated, allowing each branded user to have accessible real-time information about live digital scripts. Once the number of remaining refills is zero, the digital script is classified as complete and archived in the prescription history for the branded patient. Archived digital scripts cannot be filled by a branded pharmacist without further action by a branded provider.

Figure 8:
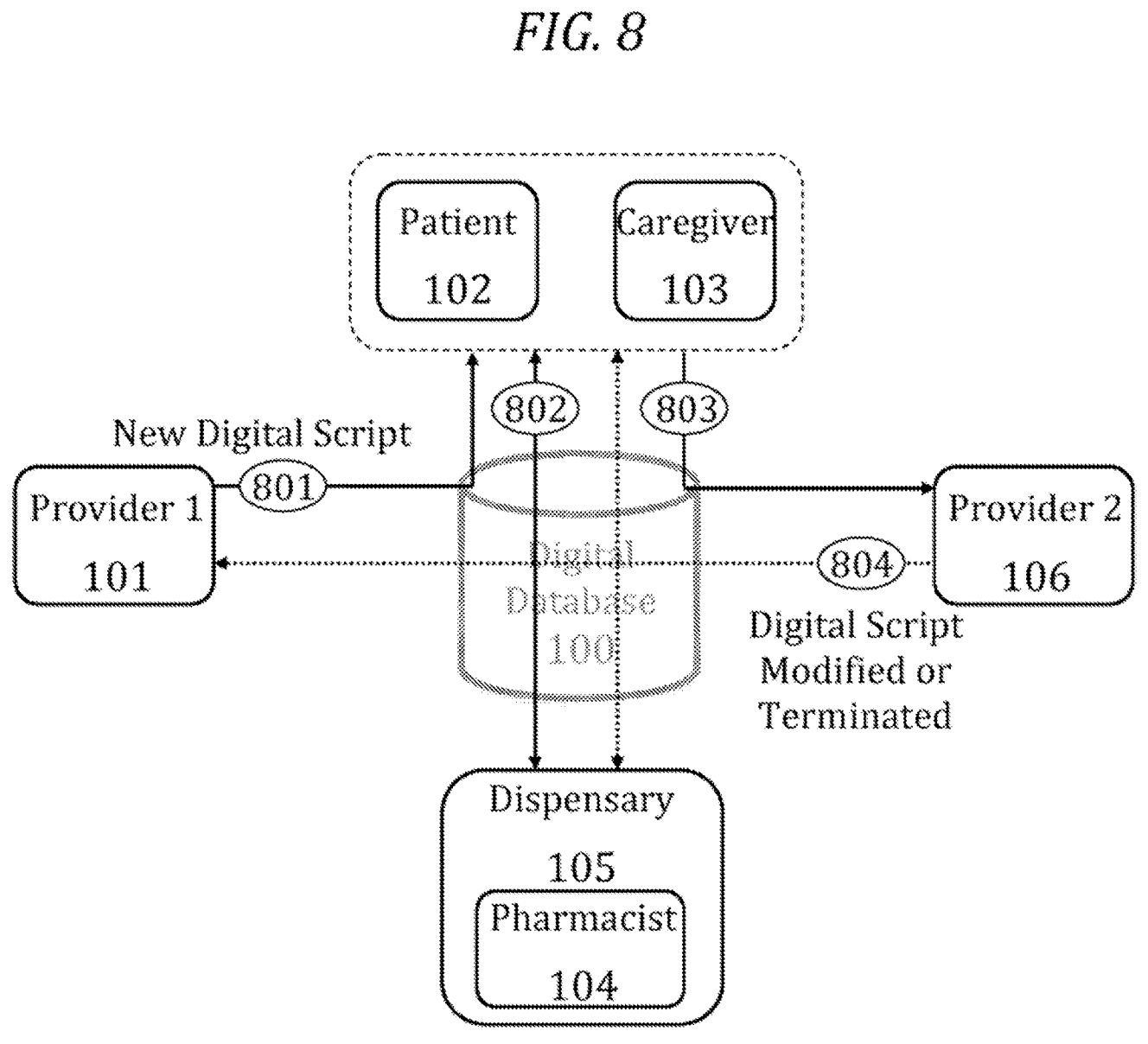

FIG. 8 is a flow diagram illustrating termination of a digital script according to some embodiments of the present invention. Unlike previous methods and systems, embodiments of the present invention allow for bidirectional flow of information regarding digital scripts. Certain embodiments allow branded providers to interact with digital scripts, even after the scripts are delivered to other branded users.

In FIG. 8, a common digital database may or may not be present in accordance with embodiments of the present invention. Beginning with step 801, a first provider 101 generates a digital script and transmits the script to a patient 102 and/or a caregiver 103. In step 802, the patient 102 and/or caregiver 103 presents the evolving digital script to a pharmacist 104 at a dispensary 105, where the script is filled with the dispensing of a prescription. In step 803, the patient presents medical information, including live digital scripts and prescription history, to a second provider 106. If the second provider 106 determines that the patient 102 should change, replace, and/or discontinue use of a particular prescription, the second provider 106 may modify or terminate the associated digital script.

A branded provider may use this feature to modify or terminate a digital script generated by the provider or to modify or terminate a digital script generated by another provider treating the same branded patient. This modification and/or termination feature may be utilized, for example, to nullify an unnecessary prescription, to prevent an undesirable prescription interaction, or to avoid undesirable side effects. In some embodiments, the termination feature is implemented simply by reducing the number of remaining refills for a digital script to zero so that the script is archived.

According to some embodiments of the present invention, when this modification and/or termination feature is used on a digital script, the provider who originally generated the digital script is notified of the reason. At step 804 in FIG. 8, the second provider 106 notifies the first provider 101, the patient 102 and/or caregiver 103, and the pharmacist 104 that the evolving digital script is being modified or terminated. If questions or concerns remain, the first provider 101 may use the system to initiate communication with the second provider 106 and even override the termination of the digital script.

Figure 9B:
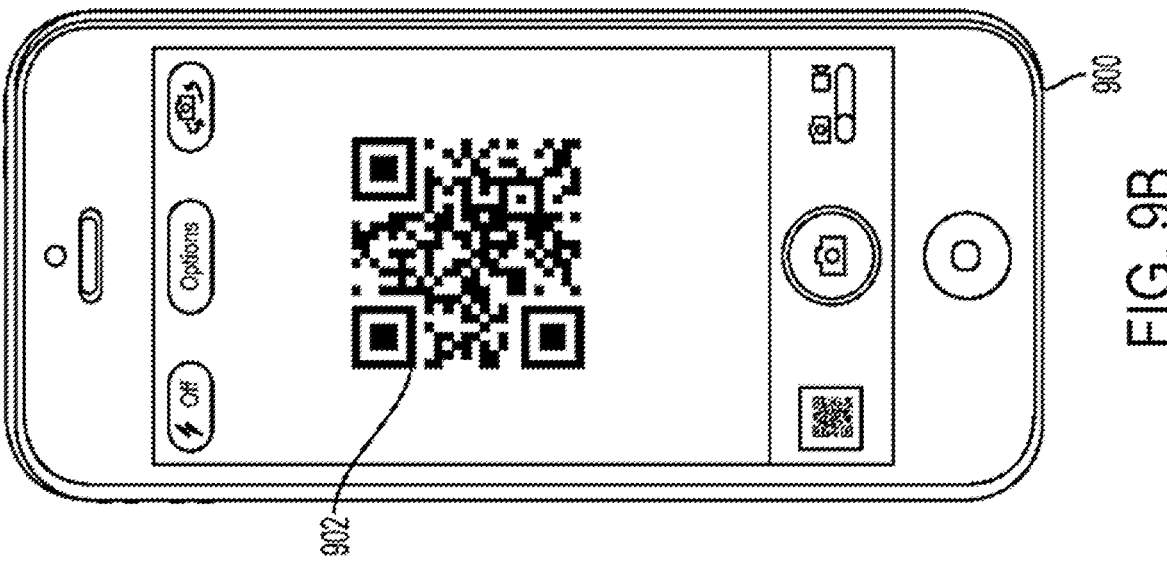
FIGS. 9A and 9B are user equipment screenshots illustrating a digital script in accordance with some embodiments of the present invention.
Figure 9A:
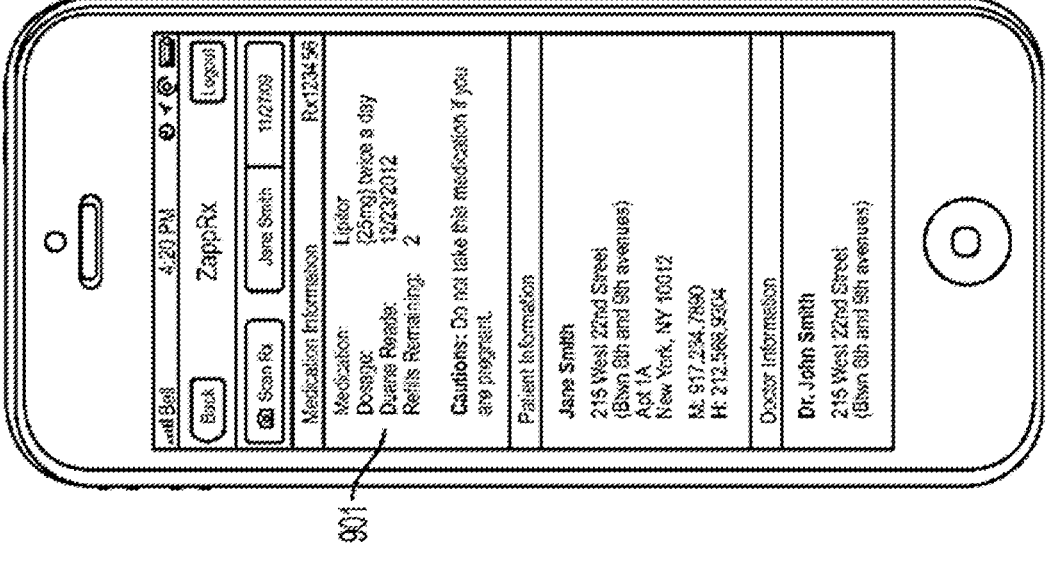

FIG. 9 depicts web interface displays on an exemplary UE 900, using two screenshots, which each feature a digital script 901, 902 in accordance with some embodiments of the present invention. As shown in FIG. 9(A), the digital script 901 contains data for a prescription requested by a health care provider. As shown in FIG. 9(B), the digital script data has been encoded in a machine-readable 2-D barcode 902, which is optimized for capture by cameras that lack auto-focus capabilities, as is the case with typical camera-enabled cellular phones. In some embodiments, a screen image similar to either screenshot in FIG. 9 displays on a branded patient's and/or branded caregiver's UE 900 when the branded patient and/or branded caregiver receives a digital script 901, 902.

In some embodiments of the present invention, a branded user accesses and interacts with the system via a prescription management software application. The application may automatically upload new and/or modified data to a dynamic, online database or other data structure. For example, a branded patient and/or branded caregiver may use a prescription management application (e.g., a GUI interface with a specific directory within a dynamic, online database) to view and/or output an available digital script via a screen image similar to either screenshot in FIG. 9. The prescription management application may further enable a branded patient and/or branded caregiver to navigate the patient's prescription history or other stored healthcare records. In preferred embodiments, the prescription management application outputs a machine-readable digital script with a human-readable prescription name or nickname. In some embodiments, a drug product prescription may be identified using a unique, three-segment number National Drug Code (NDC), which is assigned by the FDA and serves as a universal product identifier for human drugs. The use of NDC codes may improve the tracking of a patient's prescription history and the identification of potential drug interactions.

Figure 10:
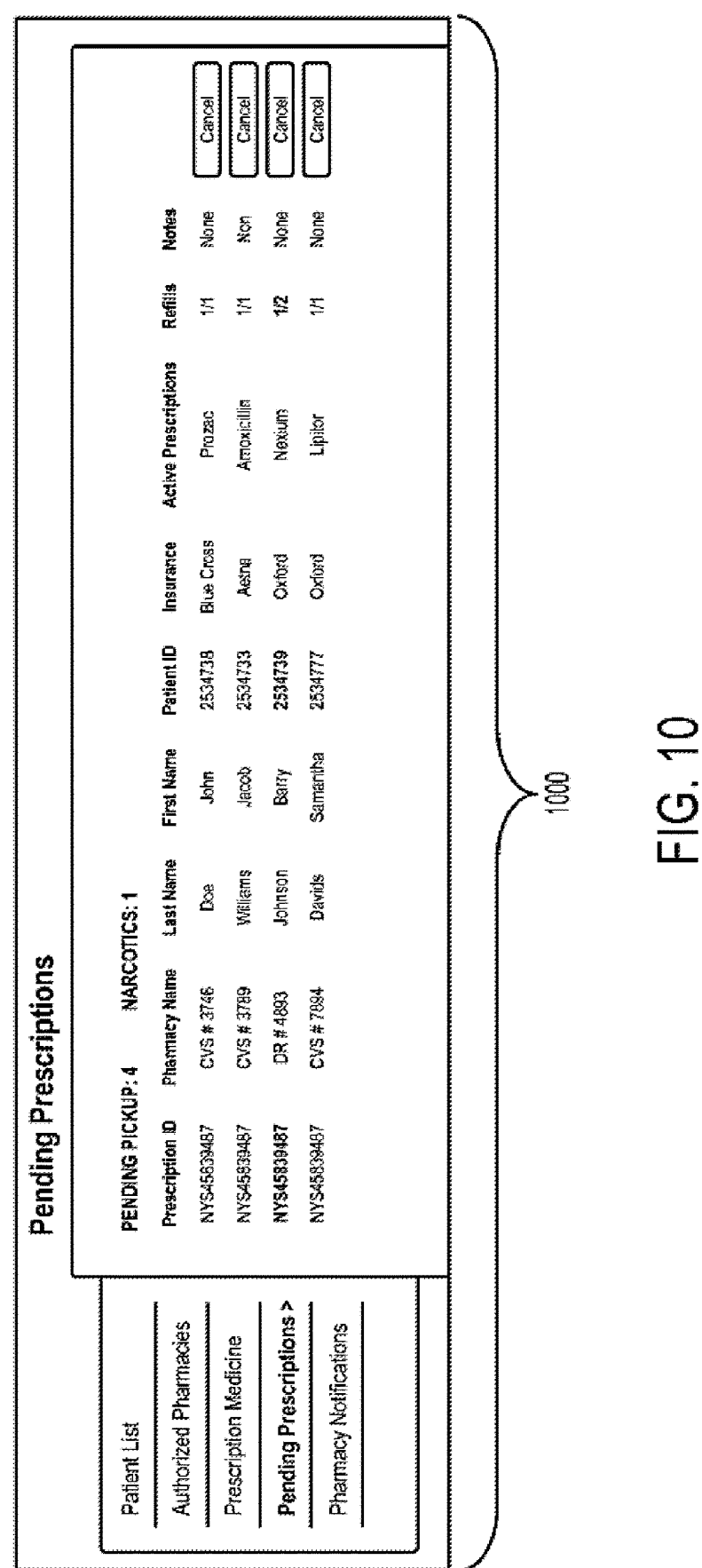
FIG. 10 is a web interface screenshot illustrating digital scripts in accordance with some embodiments of the present invention.

Similarly, FIG. 10 depicts a web interface display using a screenshot 1000, which features the GUI interface of a prescription management software application in accordance with some embodiments of the present invention. A branded provider may generate and manage multiple digital scripts for multiple patient using, for example, a screen image similar to screenshot 1000 that links to a specific directory within a dynamic, online database. In further embodiments, a branded provider may view, modify, and/or terminate a digital script for his or her patient that was generated by another branded provider. Thus, system access may be open to some extent for branded providers while being closed or limited for other branded users in accordance with some embodiments of the present invention.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the present invention is as set forth in the appended claims and equivalents thereof, rather than being limited to the examples contained in the foregoing description.

What is claimed is:

1. A method of generating, managing, and sharing a digital script in an electronic prescription system, the method comprising:

generating, by a computing device of a first branded user, a digital script for a patient, the digital script including one or more static data fields and one or more dynamic data fields, each static data field being unmodifiable by any branded user and each dynamic data field being modifiable by one or more designated branded users and being static to other branded users;

transmitting, by the computing device of the first branded user, the digital script to a computing device of a second branded user;

presenting, by the computing device of the second branded user, the digital script to a computing device of a third branded user during a script fulfillment transaction;

modifying, by the computing device of the third branded user, one or more of the dynamic data fields in the digital script that are modifiable by the third branded user to reflect completion of the script fulfillment transaction;

transmitting, by the computing device of the third branded user, the modified digital script to the computing device of the second branded user;

presenting, by the computing device of the third branded user, the modified digital script to a computing device of a fourth branded user; and terminating, by the computing device of the fourth branded user, the modified digital script based upon instructions received from the fourth branded user.

2. The method of claim 1, wherein terminating the modified digital script comprises modifying a dynamic data field of the modified digital script that comprises a number of refills remaining.

3. The method of claim 2, wherein the number of refills remaining is set to zero in order to terminate the modified digital script.

4. The method of claim 1, further comprising transmitting, by the computing device of the fourth branded user, a notification message indicating termination of the modified digital script to one or more of the computing device of the first branded user, the computing device of the second branded user, or the computing device of the third branded user.

5. The method of claim 4, wherein upon receiving the notification message, the computing device of the first branded user overrides termination of the modified digital script based upon instructions received from the first branded user.

6. The method of claim 1, wherein the digital script is stored in a digital database coupled to each of the computing devices.

7. The method of claim 6, wherein when one of the computing devices retrieves the digital script from the digital database, the digital database records an access transaction associated with the computing device for the digital script.

8. An electronic prescription system for generating, managing, and sharing a digital script, the system comprising:

a computing device of a first branded user;
a computing device of a second branded user;
a computing device of a third branded user; and
a computing device of a fourth branded user,
wherein the computing device of the first branded user is configured to:
generate a digital script for a patient, the digital script including one or more static data fields and one or more dynamic data fields, each static data field being unmodifiable by any branded user and each dynamic data field being modifiable by one or more designated branded users and being static to other branded users, and transmit the digital script to the computing device of the second branded user;

wherein the computing device of the second branded user is configured to present the digital script to the computing device of the third branded user during a script fulfillment transaction;

wherein the computing device of the third branded user is configured to:

modify one or more of the dynamic data fields in the digital script that are modifiable by the third branded user to reflect completion of the script fulfillment transaction, transmit the modified digital script to the computing device of the second branded user, and present the modified digital script to the computing device of the fourth branded user; and wherein the computing device of the fourth branded user is configured to terminate the modified digital script based upon instructions received from the fourth branded user.

9. The system of claim 8, wherein terminating the modified digital script comprises modifying a dynamic data field of the modified digital script that comprises a number of refills remaining.

10. The system of claim 9, wherein the number of refills remaining is set to zero in order to terminate the modified digital script.

11. The system of claim 8, wherein the computing device of the fourth branded user transmits a notification message indicating termination of the modified digital script to one or more of: the computing device of the first branded user, the computing device of the second branded user, or the computing device of the third branded user.

12. The system of claim 11, wherein upon receiving the notification message, the computing device of the first branded user overrides termination of the modified digital script based upon instructions received from the first branded user.

13. The system of claim 8, wherein the digital script is stored in a digital database coupled to each of the computing devices.

14. The system of claim 13, wherein when one of the computing devices retrieves the digital script from the digital database, the digital database records an access transaction associated with the computing device for the digital script.

* * * * *